(12) United States Patent
Del Soldato

(10) Patent No.: US 6,503,929 B1
(45) Date of Patent: Jan. 7, 2003

(54) NITRATE SALT OF ANTI-ULCER MEDICINE

(75) Inventor: Piero Del Soldato, Monza (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/622,068

(22) PCT Filed: Feb. 25, 1999

(86) PCT No.: PCT/EP99/01226

§ 371 (c)(1),
(2), (4) Date: Aug. 29, 2000

(87) PCT Pub. No.: WO99/45004

PCT Pub. Date: Sep. 10, 1999

(30) Foreign Application Priority Data

Mar. 5, 1998 (IT) ......................... M198A0442

(51) Int. Cl.$^7$ ................ A61K 31/4184; A61K 31/4439; C07D 401/12
(52) U.S. Cl. ..................... 514/338; 546/271; 546/273.7
(58) Field of Search .............. 546/271, 273.7, 546/338

(56) References Cited

U.S. PATENT DOCUMENTS 4,337,257 A * 6/1982 Junggren et al. ........... 546/271

FOREIGN PATENT DOCUMENTS

| DE | 23 44 779 A | 3/1974 |
|----|-------------|--------|
| EP | 0 005 129 A | 10/1979 |
| EP | 0 049 618 A | 4/1982 |
| EP | 0 224 612 A | 6/1987 |
| EP | 0 285 681 A | 10/1988 |

OTHER PUBLICATIONS

"New Guide to Medicine & Drugs", Brit. Medical Assoc. Editor, 1997, pp. 108–109.
"A Textbook of Drug Design and Development", Harwood Academic Publisher, 1991, p. 140.
"The Merck Index", Ed. 12th (1996).
Robert et al., Gastroenterology vol. 77, pp. 433–443 (1979); "Cytoprotection by Prostaglandins in Rats".

* cited by examiner

Primary Examiner—Alan L. Rotman
Assistant Examiner—Janet Coppins
(74) Attorney, Agent, or Firm—Arent Fox Kintner Plotkin & Kahn PLLC

(57) ABSTRACT

Nitrate salt compositions with anti-ulcer medicines having formula (A) and (B) wherein the (A) class compounds: $R=H$, $OCH_3$, $OCHF_2$; $R_1=CH_3$, $OCH_3$; $R_2=H$, $CH_3$; $R_3=CH_3$, $CH_2-CF_3$, $(CH_2)_3-OCH_3$; wherein the (B) class compounds: $R'_3$, $R'_4$ equal to or different from each other, are respectively free valence hydrogen, (1), $-CH_2-N(CH_3)_2$; $Y=S$, $N-R'_6$, $CR'_7R'_8$; $X=O$, $S$, $N-R'_1$; $R'_2=H$, $CH_3$; $n=0$, 1; $Z=N-CN$, $N-SO_2NH_2$, $CH-NO_2$ or formula ($VII_A$) $R'_5=H$, $-NH-CH_3$, $NH_2$; $R'_6$, $R'_7$, $R'_8$, $R'_1$, equal to or different from each other, are hydrogen, free valence. The invention also comprises the methods for the preparation of above salts.

11 Claims, No Drawings

NITRATE SALT OF ANTI-ULCER MEDICINE

The present invention relates to compositions to be used in the therapy and in the prevention of the ulcer relapses and, in general, of dyspepsias. More particularly it relates to compositions having an improved gastroprotective activity combined with a high acid secretion inhibition activity.

Products known in the art and those commercialized and used in the ulcer therapy are compounds which perform an anti-secretory activity (acid secretion inhibition). See for instance "New Guide to Medicine & Drugs" Brit. Medical Assoc. Editor, 1997, pagg. 108–109. Known products having higher therapeutic efficacy show a high anti-secretory activity and are used, both in the acute and in long-therm (six months and more) therapies. The drawback of these products is that they have a poor gastroprotectve activity, when present. From a practical point of view this means that the gastric protection is not optimal and causes inconveniences above all in the long-term therapy. In this case the presence of frequent relapses due to the enfeeblement of gastric mucosa is noticed.

To overcome these inconveniences it is known in the art to add to above medicines other anti-ulcer medicines having a gastroprotective action: prostaglandins, bismuth salts (e.g. bismuth citrate) and antibiotics. In such way the remission of ulcerous pathology is achieved. However above combinations are not satisfactory as for their tolerability in general. For example it is well known that prostaglandins produce side effects (diarrhoea) towards the intestinal tract; bismuth salts frequently produce nausea and gastric burning. Antibiotics produce unwanted gastrointestinal effects.

The need was felt to have available compositions active in the ulcer and gastric dyspepsia treatment, having improved therapeutic characteristic and tolerability, general and local, in particular having an improved gastroprotective activity combined to a high anti-secretion activity.

The Applicant has unexpectedly and surprisingly found pharmaceutical anti-ulcer compositions having the above mentioned desired properties.

It is an object of the present invention pharmaceutical compositions comprising as essential components nitrate salts of one or more components selected from the following classes of compounds:

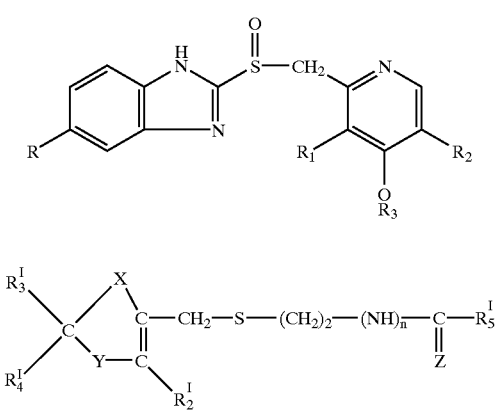

where in the (A) class compounds:
R=H, $OCH_3$, $OCHF_2$;
$R_1$=$CH_3$, $OCH_3$;
$R_2$=H, $CH_3$;
$R_3$=$CH_3$, $CH_2$—$CF_3$, $(CH_2)_3$—$OCH_3$;

where in the class (B) compounds:
$R^I_3$, $R^I_4$ equal to or different from each other, are respectively free valence, hydrogen —N=C(NH$_2$)$_2$, —CH$_2$—N(CH$_3$)$_2$;
Y=S, N—$R^I_6$, $CR^I_7 R^I_8$;
X=O, S, N—$R^I_1$;
$R^I_2$=H, $CH_3$;
n=0, 1;
Z=N—CN, N—SO$_2$NH$_2$, CH—NO$_2$ or

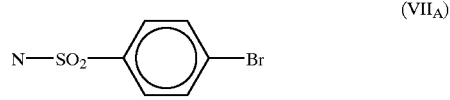

(VII$_A$)

$R^I_5$=H, —NH—CH$_3$, NH$_2$;
$R^I_6$, $R^I_7$, $R^I_8$, $R^I_1$, equal to or different from each other, are hydrogen, free valence.

The preferred nitrate salts with the (A) formula precursors are the following:
when R=$OCH_3$, $R_1$=$CH_3$, $R_2$=$CH_3$, $R_3$=$CH_3$, Omeprazole residue; as in Omeprazole, but with R=$OCHF_2$, $R_1$=$OCH_3$, $R_2$=H, Pantoprazole residue;
as in Omeprazole, but with R=H, $R_2$=H, $R_3$=(CH$_2$)$_3$—$OCH_3$, Rabeprazole residue;
as in Rabeprazole, but with $R_3$=CH$_2$—CF$_3$, Lansoprazole residue.

In the (A) class compounds also those having the following intramolecular ring are comprised, obtainable by treating the precursors in an acid aqueous environment (rif. "A Textbook of Drug Design and Development", Harwood Academic Publisher,1991, pag. 140):

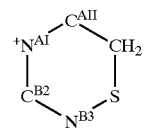

wherein $N^{AI}$ and $C^{AII}$ mean, respectively, the nitrogen and carbon atom in 1 and 2 position of the pyridine ring of formula A and $C^{B2}$ and $N^{B3}$ the carbon and nitrogen atom, respectively, in 2 and 3 position of the imydazole ring (1 position of the imydazole ring is that of the proton nitrogen).

The preferred nitrate salts with the (B) formula precursors are the following:
when in (B) formula X=N—$R^I_1$, with $R^I_1$ free valence, Y=N—$R^I_6$ with $R^I_6$=H, $R^I_3$=H, $R^I_4$ is a free valence and forms with $R^I_1$ a double bond, $R^I_2$=CH$_3$, n=1, $R^I_5$=NH—CH$_3$, Z=N—CN, Cimetidine residue;
when X=N—$R^I_1$ with $R^I_1$ free valence, Y=S, $R^I_3$=—N=C(NH$_2$)$_2$, $R^I_4$ is a free valence and forms with $R^I_1$ a double bond, $R^I_2$=H, n=1 $R^I_5$=H, Z=(VII$_A$), Ebrotidine residue;
as in Ebrotidine but with n=0, $R^I_5$=NH$_2$ and Z=N—SO$_2$NH$_2$, Famotidine residue;
as in Ebrotidine but with $R^I_3$=—CH$_2$—N(CH$_3$)$_2$, $R^I_5$=—NH—CH$_3$ and Z=CH—NO$_2$, Nizatidine residue;
as in Nizatidine, but with X=oxygen, Y=$CR^I_7 R^I_8$ with $R^I_7$ hydrogen and $R^I_8$ free valence, $R^I_4$ is a free valence and forms with $R^I_8$ a double bond, Ranitidine residue.

In the compositions according to the present invention also optical isomers of the compounds belonging to (A) and (B) classes may be used.

In the compositions according to the present invention the compound salts of above classes contain at least one mole of nitrate ion/mole of compounds. Preferably the ratio between the nitrate ion moles and the precursor is equal to one. Salts having a higher molar ratio are obtained when in the molecule other amino groups basic enough to be salified are present.

Salt precursors belonging to the above mentioned classes are prepared according to the methods described in "The Merck Index $12^a$ Ed." (1996), herein completely incorporated by reference.

The salts of the present invention may be prepared according to one of the following methods.

When the substance to be salified is available as free base or as a soluble corresponding salt in an organic solvent, which preferably does not contain hydroxyl groups, for example acetonitrile, ethyl acetate, tetrahydrofuran ecc., the salt is prepared by dissolving the substance in the solvent at a concentration preferably equal or higher than 10% w/v, by adding the amount of concentrated nitric acid corresponding to the moles of salifiable aminic groups present in the compound. The nitric acid is preferably diluted in the same solvent. Preferably during and after the addition the mixture is cooled to temperatures in the range 20°–0° C. The product is generally recovered by filtration and washed with the solvent.

When on the contrary the substance is not much soluble or it is available as a not much soluble salt in the above mentioned solvents, the corresponding mixtures with hydroxylated solvents may be used. Examples of such solvents are methyl alcohol, ethyl alcohol and water. The precipitation can be quickened by diluting then the so obtained mixture, after the addition of nitric acid, with an apolar solvent.

When the starting product is salified with hydrochloric acid it is possible to prepare the salt with nitric acid directing adding silver nitrate to the compound solution. After filtering silver chloride, the solution is concentrated and cooled to recover the nitrate salt.

When the starting product is a salt, it is possible to liberate the corresponding base by a treatment with a sodium or potassium carbonate or bicarbonate saturated solution, or with a sodium or potassium hydroxide diluted solution. The base is then extracted by a suitable organic solvent (e.g. halogenated solvents, esters, ethers) which is then dried. The organic solution is evaporated and then one proceeds according to the preceding preparation methods, by dissolving the base in acetonitrile or in the other above mentioned solvents.

It has now surprisingly been found that the compositions of the present invention allow to improve, compared with the known above mentioned combinations, the comprehensive pharmaco-toxicological situation of precursors, increasing the therapeutic efficacy and their general and local tolerability in the ulcer and gastric dyspepsia treatment with an improved gastroprotective activity.

The compositions of the present invention are formulated in the corresponding pharmaceutical compositions according to well known techniques in this field together with the common excipients; see for example the volume "Remington's Pharmaceutical Sciences 15a Ed."

The invention salt dosages are the conventional ones of their precursors of (A) and (B) classes.

It is a further object of the present invention the compositions obtainable combining one or more nitrate salts of the compounds of (A) and (B) classes, or their pharmaceutical compositions, with conventional gastroprotectives. As examples, prostaglandines, bismuth salts, active antibiotics towards pathogenic microorganisms in the gastrointestinal mucosa can be mentioned. It has surprisingly been found that gastroprotective activity of the invention compositions is very high. This makes it possible to avoid the undesirable effects of known gastroprotectives when they are used in combination with compounds or formulation of the invention. It has indeed been found that the amount of known gastroprotectives, in the combination of the invention, is lower compared with those known and does not cause undesirable effects. The skilled in this field is able to easily determine the maximum amount of conventional gastroprotectives to be combined with the pharmaceutical compositions of the invention since this corresponds to the absence of typical side effects of known gastroprotectives. In any case the amount of conventional gastroprotectives to be used in the combination is lower than that used in the combinations described in the art.

The following examples have the purpose to illustrate the invention and must not be considered as limitative of the same.

EXAMPLE 1

Preparation of Cimetidine Nitrate Salt 10 g of cimetidine are dissolved in 100 ml of an acetonitrile/tetrahydrofuran/water 1:1:2 (composition by volume) mixture cooled at +4° C. 10 ml acetonitrile solution containing 2.5 ml of 70% nitric acid are added little by little. The solution is diluted with ethyl ether, maintaining the temperature at +40° C., till to incipient precipitation of the product. After a some hour rest the precipitated solid is filtered, washed with ethyl ether and dried. 12.1 g of cimetidine mononitrate salt are recovered having m.p. 158°–159° C. (with decomposition).

$^1$H—NMR (D$_2$O): 8,55 (1H, s), 3,83 (2H, S), 3,32 (2H, s), 2,77 (3H, s), 2,68 (2H, t), 2,32 (3H, s). Elementary analysis:

| calc. (%) | C 38.09 | H 5.43 | N 31.09 | S 10.17 |
|---|---|---|---|---|
| found (%) | C 37.99 | H 5.41 | N 31.16 | S 10.25 |

Example 2

Preparation of Ranitidine Nitrate Salt 5 g of ranitidine hydrochloride are dissolved in a 140 ml acetonitrile/methyl alcohol 6:1 mixture at +20° C. 4,2 g of powder silver nitrate are added. The silver chloride precipitate is filtered, the precipitate is washed with an acetonitrile/methyl alcohol 6:1 solution, the organic phases are put together, dried and treated to obtain a dry residue. 3,5 g of an amorphous solid corresponding to the ranitidine mononitrate salt are obtained.

$^1$H—NMR (D$_2$O) :6,70 (1H, d), 6,40 (1H, d), 4,34 (2H, s), 3,83 (2H, s), 3,43 (2H, t), 2,93 (2H, m), 2,87 (9H, s).

| calc. (%) | C 41.37 | H 6.14 | N 18.56 | S 8.50 |
|---|---|---|---|---|
| found (%) | C 41.12 | H 6.20 | N 18.44 | S 8.38 |

PHARMACOLOGICAL TESTS

Example 3

Acute Toxicity

A single dose equal to 100 mg/Kg respectively of cimetidine and ranitidine nitrate salts, delt with in the previous Examples, has been given to a group of 10 rats weighing 20 g each by a cannula by oral way in a carboxymethylcellulose aqueous suspension 2% w/v.

The animals are kept under observation for 14 days. In no one of the group animals the toxic symthom presence was noted.

Example 4

Anti-ulcer Activity

Anti-ulcer activity is evaluated according to the experimental model described in the paper of A. Robert e Al. "Cytoprotection by prostaglandins in rats. Prevention of gastric necrosis produced by alcohol, HCl, NaOH, hypertonic NaCl and thermal injury" 77, 433–43 1979.

To 5 groups of 10 rats each, kept on empty stomach since the previous night, 15 minutes before the supply of absolute ethyl alcohol (1 ml), by oral way are supplied:

- 5 ml/Kg of carboxymethylcellulose aqueous suspension 2%.
- 50 mg/Kg of cimetidine in 5 ml/Kg of carboxymethylcellulose aqueous suspension 2%.
- 62,5 mg/Kg of cimetidine nitrate (corresponding to 50 mg/Kg of cimetidine) in 5 ml/Kg of carboxymethylcellulose aqueous suspension 2%.
- 50 mg/Kg of ranitidine in 5 ml/Kg of carboxymethylcellulose aqueous suspension 2%.
- 60 mg/Kg of ranitidine nitrate (corresponding to 60 mg/Kg of ranitidine) in 5 ml/Kg of carboxymethylcellulose aqueous suspension 2%.

A hour later the animals are sacrificed and the gastric lesion incidence is evaluated. Results are reported in Table 1 and they show that cimetidine and ranitidine nitrate salts have an improved gastroprotective activity compared with the corresponding starting products.

TABLE I

| Treatment | Gastric Damage % |
|---|---|
| Vehicle | 100 |
| Cimetidine | 100 |
| Cimetidine.HNO$_3$ | 50 |
| Ranitidine | 80 |
| Ranitidine.HNO$_3$ | 40 |

What is claimed is:

1. A nitrate salt of a compound chosen from the following classes:

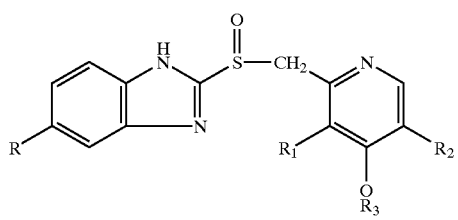

(A)

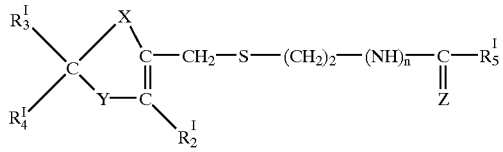

(B)

where in the compounds of formula (A):
R=OCH$_3$, R$_1$=CH$_3$, R$_2$=CH$_3$, R$_3$=CH$_3$;
R=OCHF$_2$, R$_1$=OCH$_3$, R$_2$=H, R$_3$=CH$_3$;
R=H, R$_1$=CH$_3$, R$_2$=H, R$_3$=(CH$_2$)$_3$—OCH$_3$;
R=H, R$_1$=CH$_3$, R$_2$=H, R$_3$=CH$_2$—CF$_3$;
where in formula (B):
X=N—R$^I_1$ with R$^I_1$ free valence, Y=N—R$^I_6$ with R$^I_6$=H, R$^I_3$=H, R$^I_4$ is a free valence and forms with R$^I_1$ a double bond, R$^I_2$=CH$_3$, n=1, R$^I_5$=—NH—CH$_3$, Z=N—CN;
X=N—R$^I_1$ with R$^I_1$ free valence, Y=S, R$^I_3$=—N=C(NH$_2$)$_2$, R$^I_4$ is a free valence and forms with R$^I_1$ a double bond, R$^I_2$=H, n=1, R$^I_5$=H, Z=(VII$_A$):

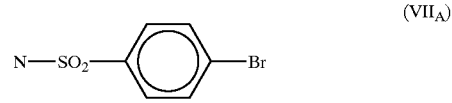

(VII$_A$)

X=N—R$^I_1$ with R$^I_1$ free valence, Y=S, R$^I_3$=—N=C(NH$_2$)$_2$, R$^I_4$ is a free valence and forms with R$^I_1$ a double bond, R$^I_2$=H, n=0, R$^I_5$=NH$_2$ and Z=N—SO$_2$NH$_2$;
X=N—R$^I_1$ with R$^I_1$ free valence, Y=S, R$^I_3$=—CH$_2$—N(CH$_3$)$_2$, R$^I_4$ is a free valence and forms with R$^I_1$ a double bond, R$_{I2}$=H, n=1, R$^I_5$=—NH—CH$_3$, Z=CH—NO$_2$;
X=oxygen, Y=CR$^I_7$R$^I_8$ with R$^I_7$ hydrogen and R$^I_8$ fee valence, R$^I_3$=—CH$_2$—N(CH$_3$)$_2$, R$^I_4$ is a free valence and forms with R$^I_7$ a double bond, R$^I_2$=H, n=1, R$^I_5$=—NH—CH$_3$, Z=CH—NO$_2$.

2. A nitrate salt of an optical isomer of a compound according to claim 1.

3. A pharmaceutical composition containing an effective amount of a nitrate salt according to claim 1 together with excipients and/or carriers.

4. A method of treating ulcers and gastric dyspepsia, said method comprising administering to a patient in need thereof an effective amount of the nitrate salts according to claim 1.

5. A composition containing a nitrate salt according to claim 1 together with conventional gastroprotective drugs.

6. Compositions according to claim 5 wherein conventional gastroprotectives are selected from prostaglandins, bismuth salts and antibiotics.

7. A method for treating ulcers and gastric dyspepsias, said method comprising administering to a patient in need thereof an effective amount of the composition of claim 5.

8. A method for the preparation of nitrate salts according to claim 1, wherein when the substance to be salified is available as free base or as a soluble corresponding salt in an organic solvent which does not contain hydroxyl groups the salt is prepared by dissolving the substance in the solvent at a concentration equal or higher than 10% w/v, by adding the amount of concentrated nitric acid corresponding to the moles of salifiable aminic groups present in the compound, by cooling during and after the addition at temperatures in the range 20° C.–0° C. and by recovering the product by filtration;

wherein when the starting material is salified with hydrochloric acid, the salt with nitric acid is prepared by directly adding silver nitrate to the compound solution, by filtering the silver chloride; the solution is then concentrated and cooled to recover the nitric salt.

9. A method for the preparation of nitrate salts according to claim 1, wherein when the starting product is a salt, the corresponding base is liberated by a treatment with a sodium or potassium carbonate or bicarbonate saturated solution or with a sodium or potassium hydroxide diluted solution, by extracting the base with a suitable organic solvent, and when the substance to be salified is available as free base or as a soluble corresponding salt in an organic solvent which does not contain hydroxyl groups the salt is prepared by dissolving the substance in the solvent at a concentration equal or higher than 10% w/v, by adding the amount of concentrated nitric acid corresponding to the moles of salifiable aminic groups present in the compound, by cooling during and after the addition at temperatures in the range 20° C.–0° C. and by recovering the product by filtration.

10. A pharmaceutical composition containing an effective amount of a composition according to claim 5 together with excipients and/or carriers.

11. The method according to claim 9, wherein when the substance is not much soluble or it is available as a not much soluble salt in the solvent containing hydroxyl groups, the corresponding mixtures with hydroxylated solvents are used and the precipitation is quickened by diluting the so obtained mixture, after the addition of nitric acid, with an apolar solvent.

* * * * *